United States Patent [19]

Braig et al.

[11] Patent Number: 5,102,457
[45] Date of Patent: Apr. 7, 1992

[54] ANTICORROSIVE SURFACE COATINGS

[75] Inventors: Adalbert Braig, Weil-Friedlingen, Fed. Rep. of Germany; Emyr Phillips, Wakefield, England

[73] Assignee: Ciba-Geigy Corp., Ardsley, N.Y.

[21] Appl. No.: 683,583

[22] Filed: Apr. 10, 1991

Related U.S. Application Data

[63] Continuation of Ser. No. 510,385, Apr. 17, 1990, abandoned.

[30] Foreign Application Priority Data

Apr. 20, 1989 [CH] Switzerland .......................... 1501/89

[51] Int. Cl.$^5$ ............................ C04B 9/02; C08K 5/13; C08K 5/15; C09D 5/8
[52] U.S. Cl. ............................ 106/14.16; 106/14.31; 106/14.37; 106/14.38; 106/14.41; 106/14.42; 106/14.43; 252/391; 428/425.8; 428/457; 428/458; 428/461; 428/462; 428/463; 428/464; 428/465; 428/467; 524/83
[58] Field of Search ............... 106/14.16, 14.31, 14.37, 106/14.38, 14.41, 14.42, 14.43; 252/391; 428/425.8, 457, 458, 461, 462, 463, 464, 465, 467; 524/83

[56] References Cited

U.S. PATENT DOCUMENTS

| | | | |
|---|---|---|---|
| 4,329,381 | 5/1982 | Eschwey et al. | 427/386 |
| 4,612,049 | 9/1986 | Berner et al. | 106/14.13 |
| 4,719,036 | 1/1988 | Clubley et al. | 252/391 |
| 4,818,777 | 4/1989 | Braig | 252/391 |
| 4,894,091 | 1/1990 | Braig et al. | 106/14.16 |

FOREIGN PATENT DOCUMENTS 60-141879 7/1985 Japan .

Primary Examiner—William R. Dixon, Jr.
Assistant Examiner—Anthony J. Green
Attorney, Agent, or Firm—JoAnn Villamizar

[57] ABSTRACT

Compounds of formula I:

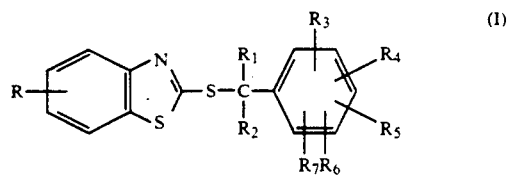

in which R, $R_1$, $R_2$, $R_3$, $R_4$, $R_5$, $R_6$ and $R_7$ are as defined in claim 1, are suitable as corrosion inhibitors in surface coatings for metals.

11 Claims, No Drawings

ANTICORROSIVE SURFACE COATINGS

This application is a continuation of application Ser. No. 510,385, filed Apr. 17, 1990 abandoned.

The invention relates to surface coatings containing S-benzylated derivatives of 2-mercaptobenzothiazole as corrosion inhibitors.

The use of 2-mercaptobenzothiazole and its salts as corrosion inhibitors for surface coatings is known e.g. from EP-A-3817. Various S-substituted derivatives of mercaptobenzothiazole have also been proposed for this purpose, e.g. carboxylic acid derivatives (EP-A-128 862) and phenolic derivatives (EP-A-259 255). S-Benzyl derivatives of mercaptobenzothiazole have been proposed as anticorrosive additives for acid metal pickling baths (JP-A-85/141 879). Metal pickling baths are aqueous solutions of acids and an added corrosion inhibitor must act at the water/metal interface. By contrast, a corrosion inhibitor in surface coatings must act at the binder/metal interface, which demands quite different physicochemical properties. It was therefore surprising to find that such S-benzyl derivatives of mercaptobenzothiazole also have an outstanding anticorrosive action on the metallic substrate when they are used in surface coatings. These derivatives are further distinguished by a good solubility in various surface coatings and do not have a detrimental effect on the adhesion of the surface coating to the metallic substrate.

The invention therefore relates to a surface coating containing, as corrosion inhibitor, at least one compound of formula I:

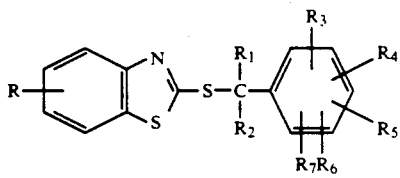

(I)

in which R is hydrogen, halogen, $C_1$-$C_{12}$ alkyl, $C_1$-$C_4$ halogenoalkyl, $C_1$-$C_{12}$ alkoxy, $C_1$-$C_{12}$ alkylthio, phenylthio, benzylthio, $C_1$-$C_{12}$ alkylsulfonyl, phenyl, —$NO_2$, —CN, —COOH, —COO($C_1$-$C_4$ alkyl), —OH, —$NH_2$, —$NHR_8$, —$N(R_8)_2$, —$CONH_2$, —$CONHR_8$ or —$CON(R_8)_2$, $R_1$ is hydrogen, $C_1$-$C_{12}$ alkyl, phenyl, phenyl substituted by halogen, $C_1$-$C_4$ alkyl, $C_1$-$C_4$ alkoxy or —$NO_2$, pyridyl, thienyl or furyl, $R_2$ is hydrogen, $C_1$-$C_4$ alkyl or phenyl, $R_3$ and $R_4$ independently of the other are H, $C_1$-$C_{20}$ alkyl, $C_1$-$C_{20}$ alkoxy, —$NO_2$, —CN, —COOH, —COO($C_1$-$C_4$ alkyl), phenyl, halogen or a group of formula II:

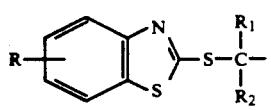

(II)

or $R_3$ and $R_4$ together are a group —CH=CH—CH=CH—, $R_5$, $R_6$ and $R_7$ are hydrogen or halogen and $R_8$ is $C_1$-$C_{12}$ alkyl, $C_3$-$C_{12}$ alkyl interrrupted by one or more —O—, $C_5$-$C_8$ cycloalkyl, benzyl, phenyl or phenyl substituted by halogen, $C_1$-$C_4$ alkyl, $C_1$-$C_4$ alkoxy or —$NO_2$, or —$N(R_8)_2$ is a pyrrolidino, piperidino or morpholino group.

In formula I, R, $R_1$, $R_2$, $R_3$, $R_4$ or $R_8$ as alkyl can be unbranched or branched alkyl, for example methyl, ethyl, n-propyl, i-propyl, n-butyl, sec-butyl, i-butyl, t-butyl, n-pentyl, sec-pentyl, n-hexyl, 2-ethylbutyl, n-octyl, 2-ethylhexyl, i-octyl, n-decyl, n-dodecyl, sec-dodecyl, n-tetradecyl, n-hexadecyl, n-octadecyl or eicosyl.

$R_8$ as alkyl interrupted by —O— can be e.g. 2-methoxyethyl, 2-ethoxyethyl, 2-butoxyethyl, 2-methoxypropyl, 3,6-dioxaheptyl, 3,6-dioxaoctyl or 3,6,9-trioxadecyl.

R as halogenoalkyl can be e.g. chloromethyl, trichloromethyl, trifluoromethyl, pentafluoroethyl or nonafluorobutyl.

$R_8$ as cycloalkyl can be e.g. cyclopentyl, cyclohexyl or cyclooctyl. R as alkoxy can be e.g. methoxy, ethoxy, isopropoxy, butoxy, hexyloxy, octyloxy or dodecyloxy. $R_3$ and $R_4$ as alkoxy can also be e.g. tetradecyloxy, hexadecyloxy or octadecyloxy. R as alkylthio can be e.g. methylthio, ethylthio, t-butylthio, octylthio or dodecylthio.

$R_1$ and $R_8$ as phenyl substituted by halogen, $C_1$-$C_4$ alkyl, $C_1$-$C_4$ alkoxy or —$NO_2$ can be e.g. tolyl, xylyl, isopropylphenyl, t-butylphenyl, chlorophenyl, dichlorophenyl, fluorophenyl, methoxyphenyl, ethoxyphenyl, butoxyphenyl or nitrophenyl.

If $R_3$ and $R_4$ together are a group —CH=CH—CH=CH—, they form a naphthyl group, which can be an α- or β-naphthyl group, together with the phenyl group to which they are bonded.

Preferred corrosion inhibitors are those of formula I in which R is hydrogen, $C_1$-$C_4$ alkyl, —$CF_3$, $C_1$-$C_4$ alkoxy, halogen, —$NO_2$, —COOH or —COO($C_1$-$C_4$ alkyl), $R_1$ is hydrogen, $C_1$-$C_4$ alkyl, phenyl or tolyl, $R_2$ is hydrogen, $C_1$-$C_4$ alkyl or phenyl, $R_3$ and $R_4$ independently of the other are H, $C_1$-$C_4$ alkyl, $C_1$-$C_4$ alkoxy, —$NO_2$, —CN, —COO($C_1$-$C_4$ alkyl), halogen or a group of formula II, or $R_3$ and $R_4$ together are a group —CH=CH—CH=CH—, and $R_5$, $R_6$ and $R_7$ are hydrogen or halogen.

Especially preferred corrosion inhibitors of formula I are those in which R is hydrogen, $C_1$-$C_4$ alkyl, $C_1$-$C_4$ alkoxy or halogen, $R_1$ is hydrogen, $C_1$-$C_4$ alkyl or phenyl, $R_2$ is hydrogen or phenyl, $R_3$ and $R_4$ independently of the other are H, $C_1$-$C_4$ alkyl, $C_1$-$C_4$ alkoxy, halogen or a group of formula II, or $R_3$ and $R_4$ together are a group —CH=CH—CH=CH—, and $R_5$, $R_6$ and $R_7$ are hydrogen or fluorine.

Preferred compounds of formula I are those in which R is hydrogen and those in which $R_1$ is hydrogen or methyl and $R_2$ is hydrogen.

Examples of compounds of formula I are:
2-benzylthiobenzothiazole,
2-(2-chlorobenzylthio)benzothiazole,
2-(4-chlorobenzylthio)benzothiazole,
2-(2-bromobenzylthio)benzothiazole,
2-(4-bromobenzylthio)benzothiazole,
2-(2-fluorobenzylthio)benzothiazole,
2-(4-fluorobenzylthio)benzothiazole,
2-(2,4-dichlorobenzylthio)benzothiazole,
2-(2,4-dibromobenzylthio)benzothiazole,
2-(2,3,4,5,6-pentachlorobenzylthio)benzothiazole,
2-(2,3,4,5,6-pentabromobenzylthio)benzothiazole,
2-(2,3,4,5,6-pentafluorobenzylthio)benzothiazole,
2-(2-methylbenzylthio)benzothiazole,
2-(4-methylbenzylthio)benzothiazole,
2-(2-methoxybenzylthio)benzothiazole,
2-(4-methoxybenzylthio)benzothiazole,
2-(2-nitrobenzylthio)benzothiazole, 2-(4-nitrobenzylthio)benzothiazole,
2-(2-cyanobenzylthio)benzothiazole,
2-(4-cyanobenzylthio)benzothiazole,
2-(diphenylmethylthio)benzothiazole,
2-(triphenylmethylthio)benzothiazole,
2-(1-naphthylmethylthio)benzothiazole,
2-(2-naphthylmethylthio)benzothiazole,
6-chloro-2-(benzylthio)benzothiazole and
5-ethoxy-2-(benzylthio)benzothiazole.

Some of the compounds of formula I are known and some are novel. The known compounds of formula I are those in which R is hydrogen, chlorine, methyl, methoxy or amino, $R_1$ and $R_2$ are hydrogen, $R_3$ and $R_4$ are hydrogen or chlorine and $R_5$, $R_6$ and $R_7$ are hydrogen.

The invention therefore further relates to compounds of formula I:

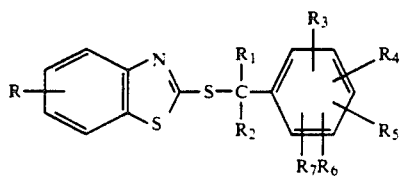

in which R is hydrogen, halogen, $C_1$-$C_{12}$ alkyl, $C_1$-$C_4$ halogenoalkyl, $C_1$-$C_{12}$ alkoxy, $C_1$-$C_{12}$ alkylthio, phenylthio, benzylthio, $C_1$-$C_{12}$ alkylsulfonyl, phenyl, —$NO_2$, —CN, —COOH, —COO($C_1$-$C_4$ alkyl), —OH, —$NH_2$, —$NHR_8$, —$N(R_8)_2$, —$CONH_2$, —$CONHR_8$ or —$CON(R_8)_2$, $R_1$ is hydrogen, $C_1$-$C_{12}$ alkyl, phenyl, phenyl substituted by halogen, $C_1$-$C_4$ alkyl, $C_1$-$C_4$ alkoxy or —$NO_2$, pyridyl, thienyl or furyl, $R_2$ is hydrogen, $C_1$-$C_4$ alkyl or phenyl, $R_3$ and $R_4$ independently of the other are H, $C_1$-$C_{20}$ alkyl, $C_1$-$C_{20}$ alkoxy, —$NO_2$, —CN, —COOH, —COO($C_1$-$C_4$ alkyl), phenyl, halogen or a group of formula II:

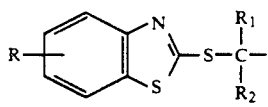

or $R_3$ and $R_4$ together are a group —CH=CH—CH=CH—, $R_5$, $R_6$ and $R_7$ are hydrogen or halogen and $R_8$ is $C_1$-$C_{12}$ alkyl, $C_3$-$C_{12}$ alkyl interrupted by one or more —O—, $C_5$-$C_8$ cycloalkyl, benzyl, phenyl or phenyl substituted by halogen, $C_1$-$C_4$ alkyl, $C_1$-$C_4$ alkoxy or —$NO_2$, or —$N(R_8)_2$ is a pyrrolidino, piperidino or morpholino group, with the exception of the compounds of formula I in which R is hydrogen, chlorine, methyl, methoxy or amino, $R_1$ and $R_2$ are hydrogen, $R_3$ and $R_4$ are hydrogen or chlorine and $R_5$, $R_6$ and $R_7$ are hydrogen.

Of these compounds of formula I, it is preferred to use
 a) those in which $R_1$ is hydrogen, $C_1$-$C_4$ alkyl or phenyl and $R_2$ is $C_1$-$C_4$ alkyl or phenyl,
 b) those in which R is —$CF_3$, —$NO_2$, —COOH or —COO($C_1$-$C_4$ alkyl), and
 c) those in which $R_3$ and $R_4$ independently of the other are $C_1$-$C_4$ alkyl, $C_1$-$C_4$ alkoxy, —$NO_2$, —CN, —Br, —F or a radical of formula II, or $R_3$ and $R_4$ together are a radical —CH=CH—CH=CH—.

The compounds can be prepared in a manner known per se by reacting a sodium mercaptide of formula III with a benzyl halide of formula IV according to the following equation:

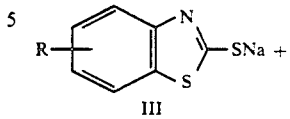

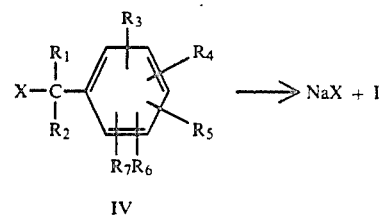

in which X is chlorine or bromine. The reaction is preferably carried out in a polar solvent, e.g. methanol, ethanol, isopropanol or dimethylformamide.

The compounds of formula I are effective corrosion inhibitors in surface coatings, examples of surface coatings being lacquers, paints or varnishes. They always contain a film-forming binder in addition to other optional components.

Examples of surface coatings are those based on an alkyd, acrylic, melamine, polyurethane, epoxy or polyester resin or mixtures of such resins. Further examples of binders are vinyl resins such as polyvinyl acetate, polyvinylbutyral, polyvinyl chloride and vinyl chloride copolymers, cellulose esters, chlorinated rubbers, phenolic resins, styrene/butadiene copolymers and drying oils. Especially preferred surface coatings are those based on an aromatic epoxy resin.

The following are examples of surface coatings with special binders:
 1. lacquers based on cold- or hot-crosslinking alkyd, acrylate, polyester, epoxy or melamine resins or mixtures of such resins, if necessary with the addition of an acid curing catalyst;
 2. two-component polyurethane lacquers based on acrylate, polyester or polyether resins containing hydroxyl groups and on aliphatic or aromatic polyisocyanates;
 3. one-component polyurethane lacquers based on blocked polyisocyanates which are unblocked during baking;
 4. two-component lacquers based on (poly)ketimines and aliphatic or aromatic polyisocyanates;
 5. two-component lacquers based on (poly)ketimines and an unsaturated acrylate resin, a polyacetoacetate resin or a methyl methacrylamidoglycolate;
 6. two-component lacquers based on polyacrylates containing carboxyl or amino groups and on polyepoxides;
 7. two-component lacquers based on acrylate resins containing anhydride groups and on a polyhydroxy or polyamino component;
 8. two-component lacquers based on (poly)oxazolidines and acrylate resins containing anhydride groups, unsaturated acrylate resins or aliphatic or aromatic polyisocyanates;
 9. two-component lacquers based on unsaturated polyacrylates and polymalonates;
 10. thermoplastic polyacrylate lacquers based on thermoplastic acrylate resins or co-reacting acrylate resins in combination with etherified melamine resins; and 11. lacquer systems based on siloxane-modified acrylate resins.

The surface coatings can be pigmented or unpigmented. The pigments can be inorganic or organic pigments or metallic pigments. Metallic pigments, e.g. aluminium pigments, are protected against corrosion by the presence of the compounds of formula I.

The surface coatings can contain an organic solvent or they can be solventless or water-based. The surface coatings can also be radiation-curable. In this case, the binder consists of monomeric or oligomeric compounds which contain ethylenic double bonds and are converted to a crosslinked high-molecular form on irradiation with actinic light or electron beams.

The surface coatings can contain further additives, e.g. fillers, flow control agents, dispersants, thixotropic agents, adhesion promoters, antioxidants, light stabilizers or curing catalysts. They can also contain other known anticorrosive agents, for example anticorrosive pigments such as pigments containing phosphate or borate or metal oxide pigments, or other organic or inorganic corrosion inhibitors, e.g. nitroisophthalic acid salts, phosphoric acid esters, technical-grade amines or substituted benzotriazoles.

It is also advantageous to add basic fillers or pigments which have a synergistic effect on corrosion inhibition in particular binder systems. Examples of such basic fillers and pigments are calcium or magnesium carbonate, zinc oxide, zinc carbonate, zinc phosphate, magnesium oxide, aluminium oxide, aluminium phosphate or mixtures thereof. Examples of basic organic pigments are those based on aminoanthraquinone.

Either the corrosion inhibitor can be added to the surface coating during its preparation, e.g. during dispersion of the pigment by grinding, or the inhibitor is first dissolved in a solvent and the solution is then stirred into the coating composition. The inhibitor is conveniently used in an amount of 0.1 to 20% by weight, preferably 0.5 to 5% by weight, based on the solids content of the surface coating. In particular cases, it may be advantageous to add several compounds of formula I.

The surface coatings are preferably used as primers for metallic substrates such as iron, steel, copper, zinc or aluminium. The surface coatings are preferably used in aqueous systems, in particular as electrophoretic enamels which can be deposited cathodically.

The surface coatings can be applied to the substrate by the conventional processes such as spraying, dipping, painting or electrodeposition, e.g. cathodic dipcoating. Several coats are often applied. The corrosion inhibitors are added primarily to the base coat because they act principally at the interface between metal and surface coating. However, it is also possible to add the inhibitors to the top coat or intermediate coat as well, where they are available as a reserve. Depending on whether the binder is a physically drying resin or a heat- or radiation-curable resin, curing is carried out at room temperature or by heating (baking) or irradiation. The following Examples describe the preparation of specific compounds of formula I and their use. Parts and percentages are by weight.

EXAMPLE 1

2-(Benzylthio)benzothiazole

A solution of 28.1 g (0.2 mol) of benzyl chloride in 50 ml of ethanol is added slowly, with stirring, to a solution of 33.4 g (0.2 mol) of 2-mercaptobenzothiazole and 8 g (0.2 mol) of NaOH in 150 ml of ethanol and 25 ml of water. The resulting solution is refluxed for 2.5 h. After cooling, it is filtered and evaporated to leave 35.1 g of a yellowish solid melting at 39°–40° C. $^1$H NMR (CDCl$_3$): δ4.41 (2H), δ6.98–7.8 (9H) ppm.

EXAMPLES 2-12

Preparation of analogous benzothiazoles

The following compounds are prepared analogously to Example 1:

| Example | Formula | M.p. | $^1$H-NMR (CDCl$_3$) |
| --- | --- | --- | --- |
| 2 | benzothiazole-S-CH$_2$-C$_6$H$_4$-F | 183–5° | 4,40 (2H), 6,65–7,85 8 (H) ppm |
| 3 | benzothiazole-S-CH$_2$-C$_6$F$_5$ | 51–2° | 4,61 (2H), 7,05–7,97 (4H) ppm |
| 4 | benzothiazole-S-CH$_2$-C$_6$H$_4$-CH$_3$ | 49–51° | 2,25 (3H), 4,50 (2H), 7,0–7,98 (8H) ppm |
| 5 | benzothiazole-S-CH$_2$-C$_6$H$_4$-OCH$_3$ | 67–8° | 3,75 (3H), 4,50 (2H), 6,77–7,92 (8H) ppm |

-continued

| Example | Formula | M.p. | $^1$H-NMR (CDCl$_3$) |
|---|---|---|---|
| 6 | 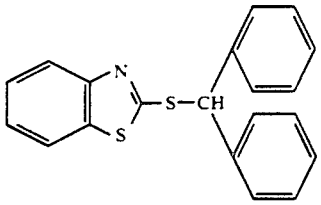 | 97–8° | 6.30 (1H), 7.10–7.90 (14H) ppm |
| 7 | 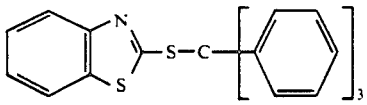 | 101–2° | 7.14–7.55 (19H) ppm |
| 8 | 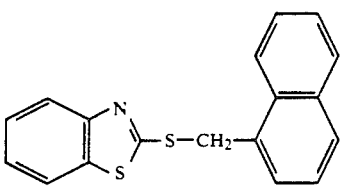 | 75–6° | 4.92 (2H), 6.99–7.99 (11H) ppm |
| 9 | 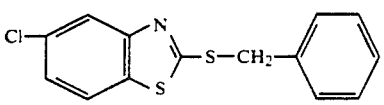 | 72–3° | 4.35 (2H), 6.82–7.63 (8H) ppm |
| 10 | 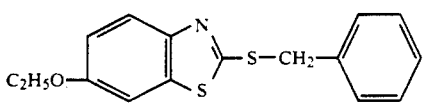 | 76–8° | 1.15 (3H), 3.80 (2H) 4.36 (2H), 6.60–7.59 (8H) |
| 11 | 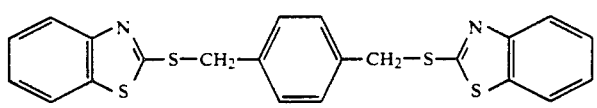 | 104–6° | 4.59 (4H), 7.21–8.0 (12H) ppm |
| 12 | 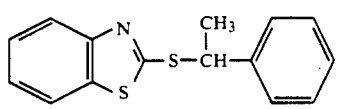 | Oil | 1.55 (3H), 4.76 (1H), 6.68–7.65 (9H) ppm |

EXAMPLE 13

Anticorrosive alkyd resin lacquer

The lacquer is prepared by mixing the following components:
- 40 parts of Alphthalat ® AM 380 alkyd resin (60% xylene solution) from Reichhold Albert Chemie AG
- 10 parts of iron oxide red 225 from Bayer AG
- 13.6 parts of talc (micronized)
- 13 parts of micronized calcium carbonate (Millicarb ®, Plüss-Staufer AG)
- 0.3 part of Luaktin ® antiskinning agent (BASF)
- 0.6 part of 8% cobalt naphthenate solution
- 24.7 parts of 6:40 xylene/propylene glycol monomethyl ether mixture.

The corrosion inhibitors shown in the following Table are first dissolved in part of the solvent and then added to the lacquer. The lacquer is ground with glass beads for 7 days until the particle size of the pigment and fillers is less than 15 μm.

The lacquer is sprayed on to 7×13 cm sandblasted steel sheets as a coat which is ca. 50 μm thick after drying. After drying for 7 days at room temperature, the test pieces are postcured for 60 minutes at 60° C.

Two 4 cm long cruciform cuts are made in the cured surface of the lacquer, down to the metal, using a Bonder cross-cutter. The edges are protected by the application of an edge protection agent (Icosit ® 255).

The test pieces are then subjected to a salt spray test according to ASTM B 117 for a period of 600 hours. After every 200 hours of weathering, the condition of the surface coating is assessed in respect of the degree of blistering (according to DIN 53 209) at the cross-cut and over the lacquered area and the degree of rusting (according to DIN 53 210) over the whole area.

When the test is complete, the surface coating is removed by treatment with concentrated sodium hydroxide solution and the corrosion of the metal is assessed at the cross-cut (according to DIN 53 167) and over the remaining area. Assessment is made in each case on a 6-point scale. The sum of the evaluation of the surface coating and the evaluation of the metal surface gives the anticorrosion value AC: the higher this value, the more effective the tested inhibitor.

| Corrosion inhibitor | Amount | Evaluation | Evlauation | AC |
| --- | --- | --- | --- | --- |
| none | — | 1,8 | 0,6 | 2,4 |
| Example 1 | 2% | 4,9 | 3,2 | 8,1 |
| Example 2 | 2% | 3,7 | 4,3 | 8,0 |
| Example 3 | 2% | 5,3 | 4,6 | 9,9 |
| Example 4 | 2% | 2,6 | 2,6 | 5,2 |
| Example 5 | 2% | 3,3 | 2,5 | 5,8 |
| Example 6 | 2% | 3,8 | 3,5 | 7,3 |
| Example 7 | 2% | 3,4 | 3,7 | 7,1 |
| Example 8 | 2% | 3,2 | 3,0 | 6,2 |
| Example 9 | 2% | 4,5 | 4,1 | 8,6 |
| Example 10 | 2% | 3,9 | 3,3 | 7,2 |
| Example 11 | 2% | 3,2 | 3,0 | 6,2 |
| Example 12 | 2% | 5,1 | 4,0 | 9,1 |

EXAMPLE 14

Anticorrosive electrophoretic enamel 217.8 g of an electrophoretic enamel are mixed with 1.5 g of propylene glycol monophenyl ether, 7.5 g of lactic acid (88%) and 1.5 g of a non-ionic wetting agent (X-Blend, Du Pont), with stirring. The electrophoretic enamel is a solution of an aromatic epoxy resin containing amino groups and hydroxyl groups and contains a capped diisocyanate as crosslinking agent. The enamel is a product from Du Pont de Nemour and has a solids content of ca. 36%.

10 g of dibutyltin dilaurate, as crosslinking catalyst, and 4 g of the corrosion inhibitor of Example 12 (2-(1-phenylethylthio)benzothiazole) are added to the above mixture and the resulting mixture is stirred to give a homogeneous solution. This corresponds to a content of 4.2% of corrosion inhibitor, based on solids.

76 g of water are initially added, with stirring. After 20 minutes, a further 76 g of water are added. After stirring for 30 minutes, a further 48 g of water are added. The emulsion formed is stirred for 48 hours and then made up with water to a volume of 1000 ml. The resulting bath has a solids content of ca. 10%. It has a pH of 4.9 and the conductivity is 2000 μS.

15×7.5 cm steel sheets are dipped into this bath as the cathode. At a bath temperature of 29° C., a voltage of 220 volts is applied for 120 seconds to deposit the enamel. The sheets are then rinsed with water, dried briefly and baked for 30 minutes at 176° C. The resulting cured enamel film has a thickness of ca. 24 μm.

For corrosion testing, a 70×0.5 mm cut is made in the surface of the sheets, which is subjected to a GM Scab Test (TM 54-26).

A test cycle consists of immersion of the test pieces for 15 minutes in a 5% aqueous NaCl solution, followed by storage for 75 minutes at room temperature and 22.5 hours in a humidity cabinet (Hot Pack Model 417522) at 60° C. and 85% relative humidity. After 5 such daily cycles, the test pieces are stored for a further 2 days in the humidity cabinet.

The sheets are then rinsed with water. The enamel which is no longer adhering firmly, due to corrosion, is mechanically removed and the average width of the corrosion zone at the cut is measured.

The average width of the corrosion zone is 7 mm for the test pieces containing the corrosion inhibitor. The average width of the corrosion zone for control test pieces without corrosion inhibitor is 31 mm.

We claim:

1. A surface coating based on an alkyd, acrylic, melamine, polyurethane, epoxy or polyester resin, mixtures of such resins, vinyl resins, cellulose esters, chlorinated rubbers, phenolic resins, styrene/butadiene copolymers or drying oils, containing, as corrosion inhibitor, at least one compound of the formula I:

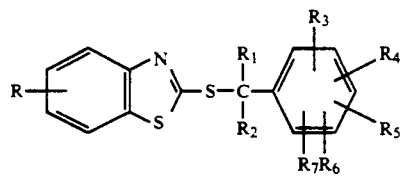

in which R is hydrogen, halogen, $C_1$-$C_{12}$alkyl, $C_1$-$C_4$-halogenoalkyl, $C_1$-$C_{12}$alkoxy, $C_1$-$C_{12}$alkylthio, phenylthio, benzylthio, $C_1$-$C_{12}$alkylsulfonyl, phenyl, —$NO_2$, —CN, —COOH, —COO($C_1$-$C_4$alkyl), —OH, —$NH_2$, —$NHR_8$, —$N(R_8)_2$, —$CONH_2$, —$CONHR_8$ or —$CON(R_8)_2$, $R_1$ is hydrogen, $C_1$-$C_{12}$alkyl, phenyl, phenyl substituted by halogen, $C_1$-$C_4$alkyl, $C_1$-$C_4$alkoxy or —$NO_2$, pyridyl, thienyl or furyl, $R_2$ is hydrogen, $C_1$-$C_4$alkyl or phenyl, $R_3$ and $R_4$ independently of the other are H, $C_1$-$C_{20}$alkyl, $C_1$-$C_{20}$alkoxy, —$NO_2$, —CN, —COOH, —COO($C_1$-$C_4$alkyl), phenyl, halogen or a group of formula II:

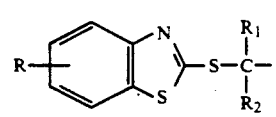

or $R_3$ and $R_4$ together are a group —CH=CH—CH=CH—, $R_5$, $R_6$ and $R_7$ are hydrogen or halogen and $R_8$ is $C_1$-$C_{12}$alkyl, $C_3$-$C_{12}$alkyl interrupted by one or more —O—, $C_5$-$C_8$cycloalkyl, benzyl, phenyl or phenyl substituted by halogen, $C_1$-$C_4$alkyl, $C_1$-$C_4$alkoxy or —$NO_2$, or —$N(R_8)_2$ is a pyrrolidino, piperidino or morpholino group.

2. A surface coating according to claim 1 containing at least one compound of formula I in which R is hydrogen, $C_1$-$C_4$ alkyl, —$CF_3$, $C_1$-$C_4$ alkoxy, halogen, —$NO_2$, —COOH or —COO($C_1$-$C_4$alkyl), $R_1$ is hydrogen, $C_1$-$C_4$ alkyl, phenyl or tolyl, $R_2$ is hydrogen, $C_1$-$C_4$ alkyl or phenyl, $R_3$ and $R_4$ independently of the other are H, $C_1$-$C_4$ alkyl, $C_1$-$C_4$ alkoxy, —$NO_2$, —CN, —COO($C_1$-$C_4$alkyl), halogen or a group of formula II, or $R_3$ and $R_4$ together are a group —CH=CH—CH=CH—, and $R_5$, $R_6$ and $R_7$ are hydrogen or halogen.

3. A surface coating according to claim 1 containing at least one compound of formula I in which R is hydrogen, $C_1$-$C_4$alkyl, $C_1$-$C_4$alkoxy or halogen, $R_1$ is hydrogen, $C_1$-$C_4$ alkyl or phenyl, $R_2$ is hydrogen or phenyl, $R_3$ and $R_4$ independently of the other are H, $C_1$-$C_4$ alkyl, $C_1$-$C_4$ alkoxy, halogen or a group of formula II, or $R_3$ and $R_4$ together are a group —CH=CH—CH=CH—, and $R_5$, $R_6$ and $R_7$ are hydrogen or fluorine.

4. A surface coating according to claim 1 containing at least one compound of formula I in which R is hydrogen.

5. A surface coating according to claim 1 containing at least one compound of formula I in which $R_1$ is hydrogen or methyl and $R_2$ is hydrogen.

6. A surface coating according to claim 1 containing 0.5 to 5% by weight, based on the solids content of the surface coating, of at least one compound of formula I.

7. A surface coating according to claim 1 which is a primer for metallic substrates.

8. A surface coating according to claim 7 which is a primer for iron, steel, copper, zinc or aluminium.

9. A surface coating according to claim 1 which is water-based.

10. A surface coating according to claim 9 which can be deposited cathodically.

11. A surface coating according to claim 1 based on an alkyd, acrylic, melamine, polyurethane, epoxy or polyester resin or a mixture of such resins.

* * * * *